(12) United States Patent
Chen

(10) Patent No.: US 9,630,859 B2
(45) Date of Patent: Apr. 25, 2017

(54) STERILIZATION APPARATUS HAVING ULTRAVIOLET LIGHT

(71) Applicants: PlayNitride Inc., Tainan (TW); Johein Technology Inc., Taipei (TW)

(72) Inventor: Cheng-Yen Chen, New Taipei (TW)

(73) Assignees: PlayNitride Inc., Tainan (TW); Johein Technology Inc., Taipei (TW)

( * ) Notice: Subject to any disclaimer, the term of this patent is extended or adjusted under 35 U.S.C. 154(b) by 0 days.

(21) Appl. No.: 14/846,844

(22) Filed: Sep. 7, 2015

(65) Prior Publication Data

US 2016/0083271 A1    Mar. 24, 2016

Related U.S. Application Data

(60) Provisional application No. 62/052,487, filed on Sep. 19, 2014.

(30) Foreign Application Priority Data

Aug. 4, 2015   (TW) .............................. 104125174 A

(51) Int. Cl.
  *A61L 2/10*   (2006.01)
  *C02F 1/32*   (2006.01)

(52) U.S. Cl.
  CPC .............. *C02F 1/325* (2013.01); *A61L 2/10* (2013.01); *C02F 2201/326* (2013.01); *C02F 2201/3222* (2013.01); *C02F 2209/005* (2013.01); *C02F 2209/42* (2013.01)

(58) Field of Classification Search
  USPC .......................... 250/453.11, 454.44, 455.11
  See application file for complete search history.

(56) References Cited

U.S. PATENT DOCUMENTS

2012/0261590 A1* 10/2012 Boyle ...................... A61L 2/10
                                                            250/453.11

FOREIGN PATENT DOCUMENTS

CN          101681963          3/2010

OTHER PUBLICATIONS

"Office Action of Taiwan Counterpart Application", issued on Dec. 17, 2015, p. 1-p. 5.

* cited by examiner

*Primary Examiner* — Nicole Ippolito
*Assistant Examiner* — Hanway Chang
(74) *Attorney, Agent, or Firm* — Jianq Chyun IP Office

(57) ABSTRACT

A sterilization apparatus having UV light capable of assembling to a container is provided. The sterilization apparatus having UV light includes a body, a light-emitting component and a heat dissipating component. The body is detachably assembled to an opening of the container to contact a fluid in the container. The light-emitting component is disposed on the body and emits UV light to irradiate the fluid in the container. The heat dissipating component is disposed in the body and is thermally coupled to the light-emitting component. The body exposes part of the heat dissipating component, such that the heat dissipating component contacts the fluid in the container.

12 Claims, 5 Drawing Sheets

STERILIZATION APPARATUS HAVING ULTRAVIOLET LIGHT

CROSS-REFERENCE TO RELATED APPLICATION

This application claims the priority benefits of U.S. provisional application Ser. No. 62/052,487, filed on Sep. 19, 2014 and Taiwan application serial no. 104125174, filed on Aug. 4, 2015. The entirety of each of the above-mentioned patent applications is hereby incorporated by reference herein and made a part of this specification.

BACKGROUND OF THE INVENTION

Field of the Invention

This invention generally relates a sterilization apparatus having ultraviolet (UV) light, and more particularly, a sterilization apparatus having UV light with a light-emitting diode (LED) as a light source.

Description of Related Art

UV light sterilization primarily utilizes UV light of an appropriate wavelength to destroy molecular structures of DNA and RNA of micro-organism cells so as to achieve sterilization effect. There are primarily four different wavebands of effective wavelength ranges of UV sterilization: VUV, of wavelengths between 100 nm and 200 nm, UVC, of wavelengths between 200 nm and 280 nm, UVB, of wavelengths between 280 nm and 315 nm, and UVA, of wavelengths between 315 nm and 400 nm.

In general, take drinking water apparatuses for instance, the interiors of drinking water apparatuses are configured with UV LED so as to provide the UV light needed to sterilize. However, the operations of UV LED cause the raise temperature in the environment which affects the dropped efficiency of light emitting. Not only is this wasteful of electricity, it also generates more heat. If the heat generated by the operation of the UV LED cannot be effectively dissipated to the exterior, the lighting efficiency is bound to drop sharply, such that the service life is reduced and the sterilization effect is diminished.

SUMMARY OF THE INVENTION

The invention provides a sterilization apparatus having UV light having good sterilization and heat dissipation effects.

The invention provides a sterilization apparatus having UV light adapted to being assembled to a container. The sterilization apparatus having UV light includes a body, a light-emitting component, and a heat dissipation component. The body is detachably assembled to an opening of the container so as to contact a fluid in the container. The light-emitting component is disposed on the body and emits UV light to irradiate the fluid in the container. The heat dissipation component is disposed in the body and is thermally coupled to the light-emitting component. Part of the heat dissipation component is exposed from the body so as to contact the fluid in the container.

In an embodiment of the invention, the above described sterilization apparatus having UV light further includes a switch component. The switch component is disposed on the body and is electrically coupled to the light-emitting component. When the body is assembled to the opening of the container, the container actuates the switch component.

In an embodiment of the invention, the above described sterilization apparatus having UV light further includes a controller and a sensing module. The controller is disposed on the body and is electrically coupled to the switch component and the light-emitting component, so as to control the light-emitting component to emit a UV light. The sensing module is disposed on the body and electrically coupled to the controller.

In an embodiment of the invention, the above-described sensing module includes a motion sensor, so as to detect the inclination state of the body after being assembled to the container.

In an embodiment of the invention, the above described motion sensor includes a G-sensor.

In an embodiment of the invention, the above described motion sensor includes an orientation sensor.

In an embodiment of the invention, the above described sensing module includes a fluid sensor so as to detect whether fluid is stored in the container.

In an embodiment of the invention, the above described sensing module includes a fluid level sensor configured to detect the fluid level of the container.

In an embodiment of the invention, the sterilization apparatus having UV light further includes a positioning component. The positioning component is connected to the body. The body is disposed between the positioning component and the light-emitting component. The positioning component has at least a positioning portion. The positioning portion is located at a side of the body. When the body is assembled to the opening of the container, part of the container close to the opening is disposed between the positioning portion and the body.

In an embodiment of the invention, the above described sterilization apparatus having UV light further includes a transparent cover. The transparent cover covers a recess of the body, wherein the light-emitting component is located in the recess, and the UV light emitted by the light-emitting component is adapted to pass through the transparent cover so as to radiate the fluid in the container.

In an embodiment of the invention, the above described heat dissipation component includes a first end portion connected to the light-emitting component and a second end portion contacting the fluid.

In an embodiment of the invention, the ratio between the surface area of the first end portion exposed in the recess and the area where the light-emitting component contacts the first end portion is less than 20.

In an embodiment of the invention, the ratio between the area where the body contacts the fluid and the area where the second end portion contacts the fluid is less than 20.

Based on the above, the sterilization apparatus having UV light of the invention is capable of conducting the heat generated from operation of the light-emitting component to the fluid in the container via the heat dissipation component, so as to reduce the operation temperature of the light-emitting component and increase the light-emitting efficiency of the light-emitting component. On the other hand, the fluid in the container generates convection flow due to the heat. As a result, the UV emitted by the light-emitting component can uniformly irradiate the fluid in the container, so as to destroy bacteria or other micro-organism in the fluid.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
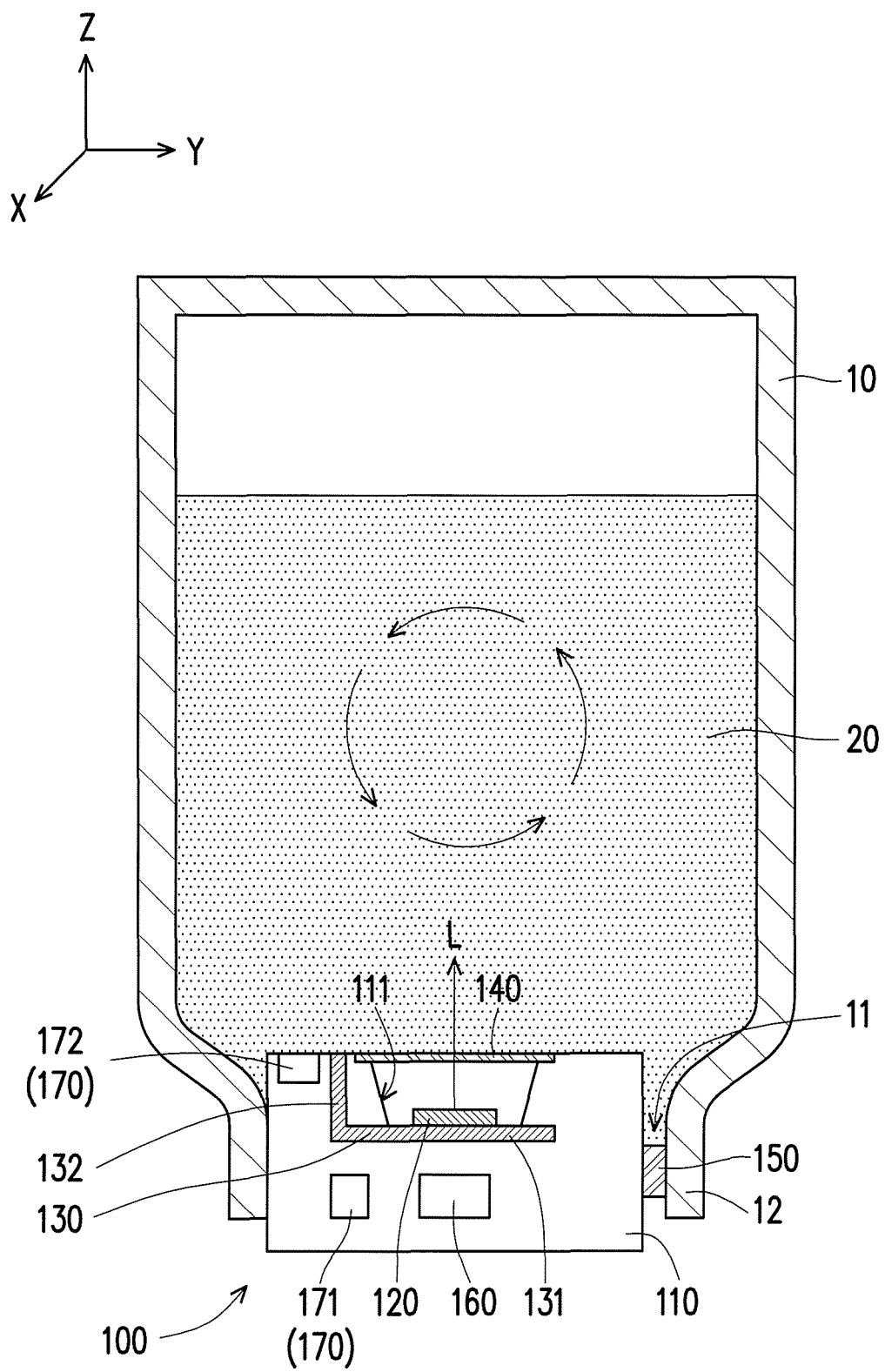
FIG. 1 is a schematic of the sterilization apparatus having UV light of an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a diagram illustrating the sterilization apparatus having UV light of an embodiment of the invention. Referring to FIG. 1, in the present embodiment, a sterilization apparatus having UV light 100 is adapted to being assembled to a container 10 so as to sterilize a fluid 20 of the container 10. For instance, the container 10 may be a portable water bottle or another similar container, and the fluid 20 may be water, milk, juice, or other fluid.

The sterilization apparatus having UV light 100 includes a body 110, a light-emitting component 120, and a heat dissipation component 130. The body 110 may be made of, for instance, waterproof material, and is capable of being detachably assembled to an opening 11 of the container 10. The body 110 may include a recess 111. The light-emitting component 120 is disposed on the body 110 and is located in the recess 111. The light-emitting component 120 may be at least one UV LED. Compare to a known mercury lamp, the UV LED is smaller and therefore allowing the sterilization apparatus having UV light 100 to meet miniaturization design demands, thus beneficial for portable use by users. The light-emitting component 120 is adapted to emit an UV light L of wavelength between 200 nm and 400 nm. Preferably, the light-emitting component 120 is adapted to emit an UV light L of wavelength between 200 nm and 280 nm, i.e., UVC. Since micro-organism cells absorb UV light of wavelength between 260 nm to 280 nm better, the sterilization effect is better. Here, a wall surface of the recess 111 may be coated with highly reflective material or highly scattering material, such that the UV light L emitted by the light-emitting component 120 can be effectively reflected or scattered toward the fluid 20. FIG. 1 illustrates the heat dissipation component 130 and a light-emitting component 120. In another embodiment, there may be a plurality of the heat dissipation components 130 and the light-emitting components 120.

On the other hand, the heat dissipation component 130 is disposed in the body 110 and thermally coupled to the light-emitting component 120. The heat dissipation component 130 may be for instance embedded in the body 110, wherein the heat dissipation component 130 includes a first end portion 131 connected to the light-emitting component 120 and a second end portion 132 contacting the fluid 20. More particularly, the first end portion 131 may be partially exposed at the bottom of the recess 111 so as to connect to the light-emitting component 120. The second end portion 132 may be partially exposed from the wall surface where the body 110 being in contact with the fluid 20 of the container 10, so as to contact the fluid 20. For instance, the first end portion 131 of the heat dissipation component 130 may be a circuit board coated with a high conductivity material layer, wherein the layer material of high conductivity may be copper, aluminum, or other metal or alloy of good conductivity, or high molecular material of good conductivity such as diamond-like carbon or nano carbon. The second end portion 132 may be of a high conductivity material, e.g., copper, aluminum, or other metal or alloy with good conductivity, or high molecular material of good conductivity such as diamond-like carbon or nano carbon. In the present embodiment, the second end portion 132 may be, for instance, integrally formed with the first end portion 131. In another embodiment, the second end portion 132 may be assembled to the first end portion 131 by means such as soldering, adhering, locking, or engaging. The invention does not impose a restriction.

When disposed as such, heat generated from operation of the light-emitting component 120 can be conducted from the heat dissipation component 130 to the fluid 20 via thermal coupling, so as to lower an operation temperature of the light-emitting component 120, such that lighting efficiency of the light-emitting component 120 does not drop due to the raise of the operation temperature, and the lighting efficiency of the light-emitting component 120 is improved. On the other hand, the fluid 20 is disrupted by the convection flow in the container 10 caused by the conducting of heat from the heat dissipation component 130 to the fluid 20, such that the the fluid 20 can be evenly irradiated by the UV light L emitted by the light-emitting component 120, killing bacteria or other micro-organism in the fluid 20. Note particularly that the ratio between the surface area of the first end portion 131 exposed in the bottom of the recess 111 and the area where the light-emitting component 120 being contact with the first end portion 131 is less than 20. Preferably, the ratio is less than 10. In other words, increasing the area where the light-emitting component 120 being contact with the first end portion 131 helps raising the efficiency of conducting heat generated by the light-emitting component 120 to the heat dissipation component 130. On the other hand, the ratio between the area where the wall surface of the body 110 being contact with the fluid 20 and the area where the second end portion 132 being contact with the fluid 20 is less than 20. Preferably, the ratio is less than 10. In other words, increasing the area where the second end portion 132 being contact with the fluid 20 helps improving the efficiency of conducting of heat generated by the light-emitting component 120 to the fluid 20, so as to enhance effects of the convection flow of the fluid 20.

In the present embodiment, the sterilization apparatus having UV light 100 further includes a transparent cover 140. The transparent cover 140 covers the recess 111 of the body 110. For instance, the transparent cover 140 may be bonded to the body 110 via waterproof glue, or by disposing a sealing element at the junction between the transparent cover 140 and the body 110, so as to prevent the fluid 20 from entering the recess 111. As a result, when the body 110 is assembled to the opening 11 of the container 10, the transparent cover 140 contacts the fluid 20, and the UV light L emitted by the light-emitting component 120 is adapted for penetrating through the cover 140 so as to irradiate the fluid 20. Here the transparent cover 140 is in a flat form, but in an embodiment (not in the drawings), the transparent cover is capable of having corresponding optical designs depending on differences in the container 10, so as to enable the UV light L emitted by the light-emitting component 120 to irradiate the fluid 20 more evenly after penetrating through the transparent cover 140. For instance, if the container 10 is cylinder-shaped, the transparent cover 140 may be a concave lens, so as to allow the UV light L to irradiate the fluid 20 more dispersively and more evenly after penetrating through the transparent cover 140. If the container 10 is tubular-shaped, the transparent cover 140 may be a convex lens, so as to allow the UV light L to irradiate the fluid 20 more focusedly after penetrating through the transparent cover 140.

Figure 2:
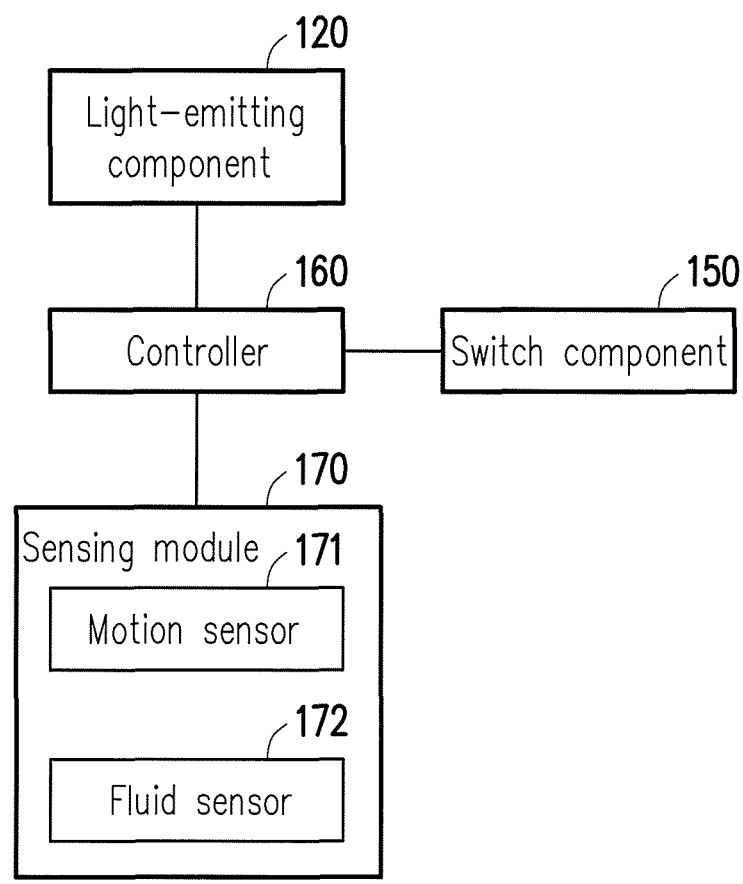
FIG. 2 is a schematic of the circuit of the sterilization apparatus having UV light of FIG. 1.

FIG. 2 is a diagram illustrating the circuit of the sterilization apparatus having UV light of FIG. 1. Referring to FIG. 1 and FIG. 2, the sterilization apparatus having UV light 100 further includes a switch component 150, e.g., a mechanical switch. The switch component 150 is disposed on a side of the body 110 and is electrically coupled to the light-emitting component 120. When the body 110 is assembled to the opening 11 of the container 10, an end portion 12 that defines the opening 11 actuates the switch component 150, so as to cause a supplied power (e.g., a battery. Not in the drawings) disposed on the body 110 to be turned on so as to control the switch of the light-emitting component 120. Note particularly that at this time the sterilization apparatus having UV light 100 and the container 10 are sealed, such that the fluid 20 of the container 10 does not flow out from the junction between the sterilization apparatus having UV light 100 and the container 10. More particularly, the sterilization apparatus having UV light 100 further includes a controller 160 and a sensing module 170. The controller 160 and the sensing module 170 are respectively disposed on the body 110, wherein the controller 160 is electrically coupled to the switch component 150 and the light-emitting component 120. More specifically, the switch component 150 may be, for instance, electrically coupled to the light-emitting component 120 via the controller 160. Hence, the light-emitting component 120 does not emit the UV light L immediately when the container 10 actuates the switch component 150, but instead is controlled by the controller component 160. When the container 10 actuates the switch component 150, the operation mechanics of whether the light-emitting component 120 emits the UV light L is explained below.

The sensing module 170 is electrically coupled to the controller 160. The sensing module 170 is adapted to detect the inclination state of the body 110 and detect whether the fluid 20 is stored in the container 10. In the present embodiment, the sensing module 170 includes a motion sensor 171 and a fluid sensor 172. The motion sensor 171 may be a G-sensor or an orientation sensor configured to detect the inclination state of the body 110 after being assembled to the container 10. More specifically, the G-sensor can detect the gravitational components of the X axis, Y axis, and the Z axis of the body 110, and the orientation sensor can detect the variation amount of rotation angle of the X axis, Y axis, and the Z axis of the body 110, so as to ensure the body 110 is not assembled to the container 10 in a tilted state such that the fluid 20 to be atop of the body 110. In this way, the UV light L emitted to by the light-emitting component 120 can irradiate the fluid 20 without being skewed. In other words, through the sensing of the motion sensor 171, it can be ensured that an optical axis of the UV light L emitted by the light-emitting component 120 can be ensured to parallel to a normal vector of a cross section of an opening of the container 10, thus preventing an oblique emission of the UV light L from the container 10 that causing uneven sterilization or harm to a human body. Moreover, the fluid sensor 172 can be configured to detect whether the fluid 20 is stored in the container 10 via a contact or non-contact detection method. Here, the fluid sensor 172 is, for instance, a contact fluid sensor determining whether the fluid 20 is stored in the container 10 based on physical or chemical changes directly generated when the fluid sensor 172 and the fluid 20 are in contact.

After the motion sensor 171 detects the fluid 20 is atop of the body 110, and the fluid sensor 172 detects the fluid 20 is stored in the container 10, the motion sensor 171 and the fluid sensor 172 respectively transmit sensor signals to the controller 160. The controller 160 transmits a corresponding control signal to the light-emitting component 120 after receiving the above-described signals, so as to control the light-emitting component 120 to emit the UV light L to irradiate the fluid 20 of the container 10. This type of error proofing mechanism prevents the body 110 from being tilted on the container 10 (i.e., the fluid 20 is not atop of the body 110) or the UV light L emitting from light-emitting component 120 when the fluid 20 is not in the container 10, even irradiating the user. As a result, the risk to the user is significantly reduced when operating the sterilization apparatus having UV light 100.

Below are other embodiments for illustration. It must be noted that the embodiments below follow the component labeling and parts of the contents of the above described embodiments, wherein identical labeling are used to indicate identical or similar components, and explanations on identical technical contents are therefore omitted. The embodiments below do not repeat identical or similar technical contents. Refer to the embodiments above for explanation of the omitted parts.

Figure 3:
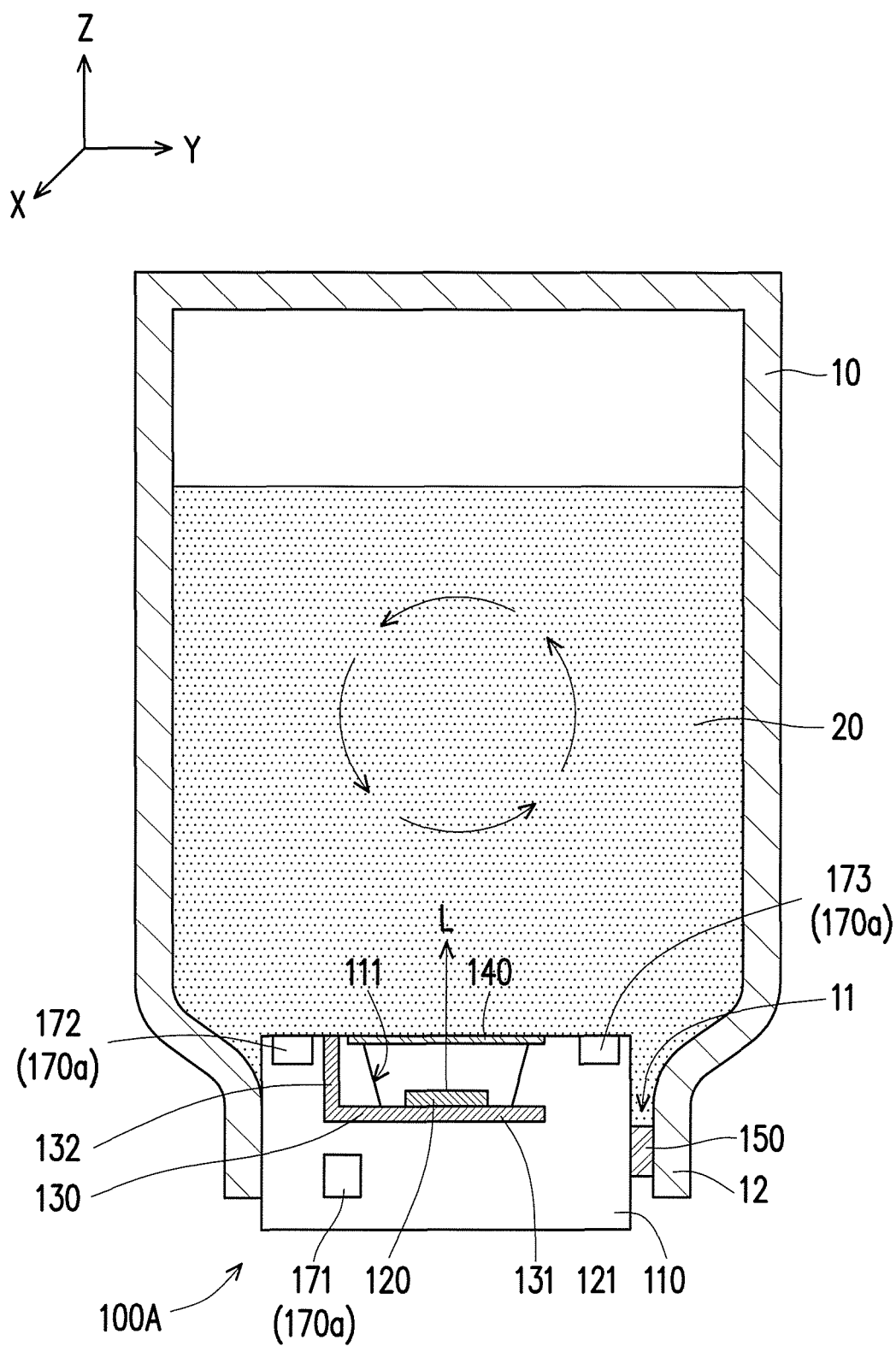
FIG. 3 is a schematic of the sterilization apparatus having UV light of another embodiment of the invention.
Figure 4:
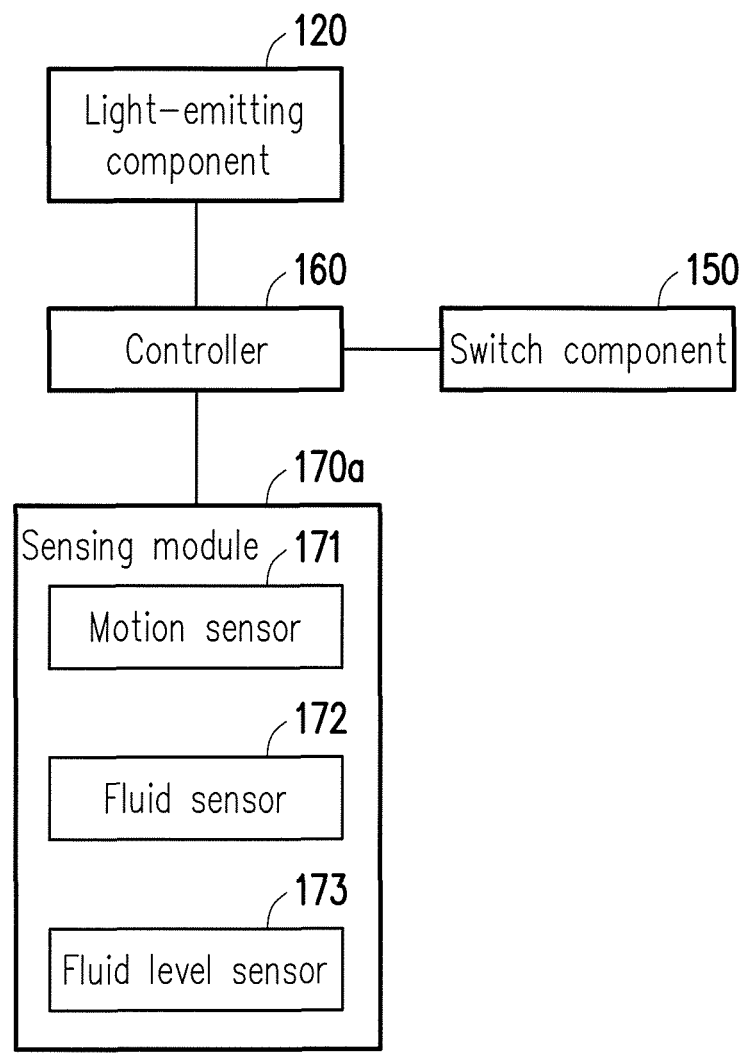
FIG. 4 is a schematic of the circuit of the sterilization apparatus having UV light of FIG. 3.

FIG. 3 is a diagram illustrating the sterilization apparatus having UV light of another embodiment of the invention. FIG. 4 is a diagram illustrating the circuit of the sterilization apparatus having UV light of FIG. 3. Referring to FIG. 3 and FIG. 4, a sterilization apparatus having UV light 100A of the present embodiment is similar to the sterilization apparatus having UV light 100 above with the main difference being: a sensor 170a of the sterilization apparatus having UV light 100A further includes a fluid level sensor 173. That is to say, the sensing module 170a not only is able to detect the inclination state of the body 110 and detect fluid 20 in the container 10, it can also detect the level of the fluid 20 of the container 10.

More specifically, the fluid level detector 173 may be a pressure sensor able to calculate the level of the fluid 20 of the container 10 using the pressure applied to the body 110 by the fluid 20 of the container 10. For instance, a detected pressure value may be a corresponding level calculated directly by the fluid level sensor 173, and then the calculated level is transmitted to the controller 160. Another way is to transmit the detected pressure value to the controller 160, and then the controller 160 calculates the corresponding level. This way, the controller 160 is able to control the operation time (i.e., the time the UV light L irradiates the fluid 20 of the container 10) of the light-emitting component 120 based on the level of the fluid 20 of the container 10, so as to effectively sterilize the fluid 20 of the container 10 and help conserve electrical power. In another embodiment, the fluid level sensor 173 may be a charge-coupled device, that calculates the level of the fluid 20 of the container 10 through detecting an image of the fluid 20 or the container 10. Note particularly that the fluid level sensor 173 and the fluid sensor 172 may be integrated into a single module capable of detecting fluid 20 of the container 10 and the level of the fluid 20 at the same time, making the sterilization apparatus having UV light 100A more convenient for the user to carry.

Figure 5:
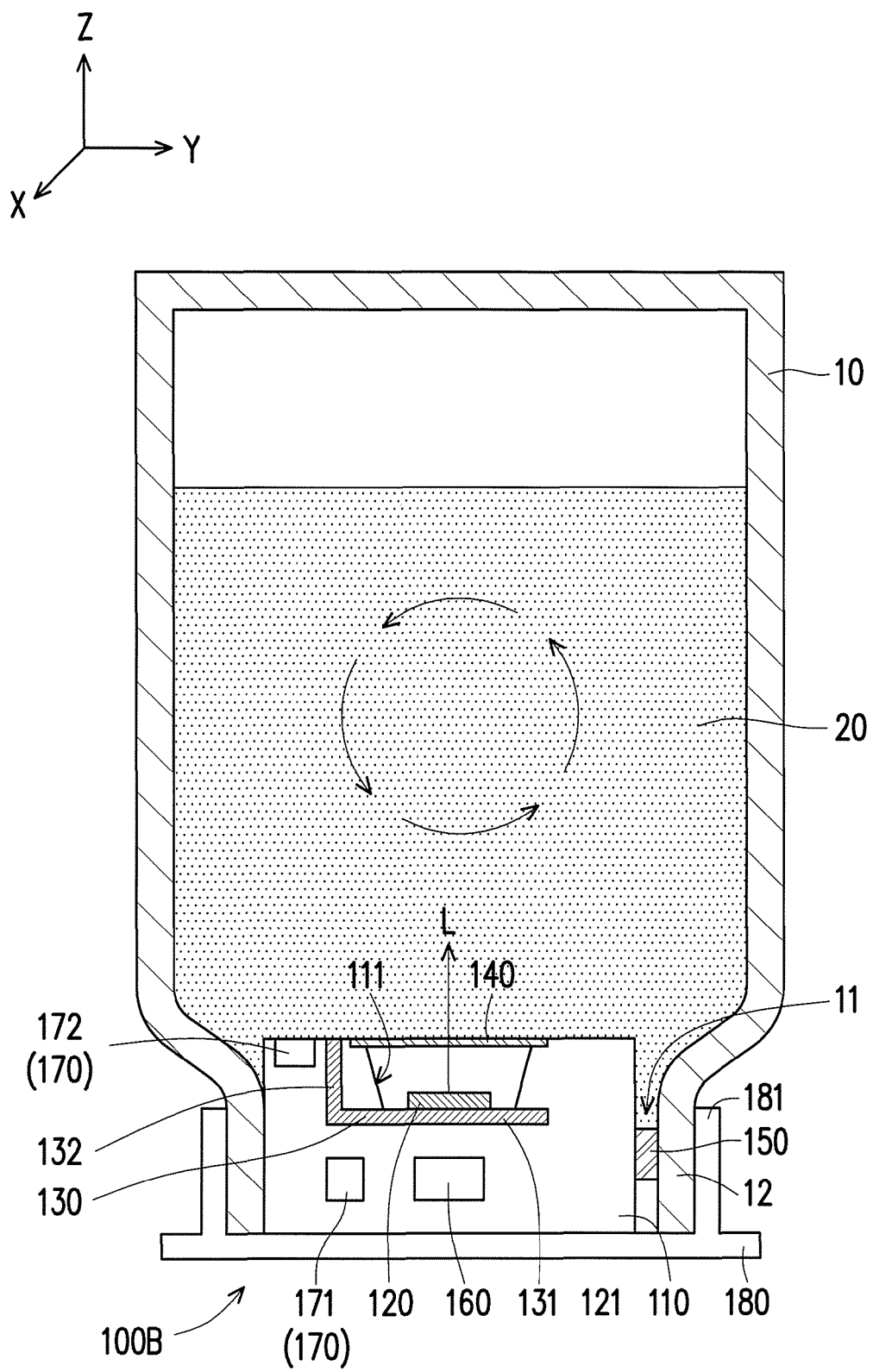
FIG. 5 is a schematic of the sterilization apparatus having UV light of yet another embodiment of the invention.

FIG. 5 is a diagram illustrating the sterilization apparatus having UV light of another embodiment of the invention. Refer to FIG. 5, a sterilization apparatus having UV light 100B of the present embodiment is similar to the sterilization apparatus having UV light 100 above with the main difference being: the sterilization apparatus having UV light 100B further includes a positioning component 180 in order to securely assemble the body 110 and the container 10.

More specifically, the positioning component 180 is connected to the body 110, and the body 110 is located between the positioning component 180 and the light-emitting component 120. On the other hand, the positioning component 180 has at least a positioning portion 181 (two are illustrated by FIG. 5) and is located at a side of the body 110. In another embodiment, the positioning portion may be a ring-shaped structure. The invention does not particularly limit the geometric shape of the positioning part. When the body 110 is assembled to the opening 11 of the container 10, the end portion 12 may be for instance located between the positioning portion 181 and the body 110. In other words, when the body 110 is assembled to the opening 11 of the container 10, the end portion 12 of the container 10 abuts the positioning component 180 and is clamped between the positioning portion 181 and the body 110, thereby increase the stability when the body 110 and the container 10 are assembled. For instance, the positioning component 180 has non-slip effects using, for instance, using non-slip material or forming non-slip patterns on a surface area of the positioning component 180 (e.g., roughening the surface area) to prevent easy separation of the assembled sterilization apparatus having UV light 100B and the container 10.

Based on the above, the sterilization apparatus having UV light of the invention is capable of conducting the heat generated from operation of the light-emitting component to the fluid in the container via the heat dissipation component, in order to reduce the operation temperature of the light-emitting component and increase the light-emitting efficiency of the light-emitting component. On the other hand, the fluid in the container generates convection flow due to the heat. As a result, the UV light emitted by the light-emitting component is able to irradiate the fluid in the container evenly, so as to destroy bacteria or other microorganism in the fluid.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A sterilization apparatus having UV light adapted to being assembled to a container with a liquid therein, comprising:
    a body, detachably assembled to an opening of the container, so as to be in contact with the liquid in the container;
    a light-emitting component, disposed on the body and emits UV light to irradiate the liquid in the container; and
    a heat dissipation component, disposed in the body and thermally coupled to the light-emitting component, wherein part of the heat dissipation component is exposed from the body so as to contact the liquid in the container, and the heat dissipation component comprises a first end portion connected directly to the light-emitting component and a second end portion directly contacting the liquid.

2. The sterilization apparatus having UV light as claimed in claim 1, further comprising:
    a switch component, disposed on the body and electrically coupled to the light-emitting component, wherein when the body is assembled to the opening of the container, the container actuates the switch component.

3. The sterilization apparatus having UV light as claimed in claim 2, further comprising:
    a controller, disposed on the body, electrically coupled to the switch component and the light-emitting component and configured to control the light-emitting component to emit the UV light; and
    a sensing module, disposed on the body and electrically coupled to the controller.

4. The sterilization apparatus having UV light as claimed in claim 3, wherein the sensing module comprising a motion sensor so as to detect the inclination state of the body after being assembled to the container.

5. The sterilization apparatus having UV light as claimed in claim 4, wherein the motion sensor further comprising a gravity sensor.

6. The sterilization apparatus having UV light as claimed in claim 4, wherein the motion sensor comprises an orientation sensor.

7. The sterilization apparatus having UV light as claimed in claim 3, wherein the sensing module comprises a liquid sensor so as to detect whether the liquid is stored in the container.

8. The sterilization apparatus having UV light as claimed in claim 3, wherein the sensing module comprises a liquid level sensor so as to detect liquid level in the container.

9. The sterilization apparatus having UV light as claimed in claim 1, further comprising:
    a positioning component, connected to the body, the body is located between the positioning component and the light-emitting component, the positioning component having at least a positioning portion located at a side of the body, and when the body is assembled to the opening of the container, part of the container close to the opening is disposed between the positioning portion and the body.

10. The sterilization apparatus having UV light as claimed in claim 1, further comprising:
    a transparent cover, covering a recess of the body, wherein the light-emitting component is located in the recess and the UV light emitted by the light-emitting component is adapted to pass through the transparent cover so as to radiate the liquid in the container.

11. The sterilization apparatus having UV light as claimed in claim 1, wherein a ratio between a surface area of the first end portion exposed in the recess and an area where the light-emitting component being in contact with the first end portion is less than 20.

12. The sterilization apparatus having UV light as claimed in claim 1, wherein a ratio between an area where the body being in contact with the liquid and an area where the second end portion being in contact with the liquid is less than 20.

* * * * *